United States Patent [19]

Sinofsky et al.

[11] Patent Number: 4,878,492
[45] Date of Patent: Nov. 7, 1989

[54] LASER BALLOON CATHETER

[75] Inventors: Edward L. Sinofsky, N. Reading, Mass.; J. Richard Spears, Bloomfield Hills, Mich.; Douglas W. Dickinson, Merrimack, N.H.; Maria S. Wagner, Reading, Mass.

[73] Assignee: C. R. Bard, Inc., Murray Hill, N.J.

[21] Appl. No.: 106,609

[22] Filed: Oct. 8, 1987

[51] Int. Cl.⁴ ............................................. A61B 17/36
[52] U.S. Cl. ................................. 128/303.1; 128/395
[58] Field of Search ....................... 128/4–8, 128/303.1, 395–398; 252/301.17

[56] References Cited

U.S. PATENT DOCUMENTS

| | | | |
|---|---|---|---|
| 3,467,098 | 9/1969 | Ayres | 128/303.1 |
| 3,617,109 | 11/1971 | Tien | 350/96 |
| 3,670,721 | 6/1972 | Fukami et al. | 128/6 |
| 4,060,308 | 11/1977 | Barnoski et al. | 350/96 C |
| 4,195,637 | 4/1980 | Gruntzig | 128/348 |
| 4,420,796 | 12/1983 | Mori | 362/32 |
| 4,445,751 | 5/1984 | Divens et al. | 350/96.14 |
| 4,470,407 | 9/1984 | Hussein et al. | 128/6 |
| 4,506,368 | 3/1985 | Lee | 252/301.17 |
| 4,512,762 | 4/1985 | Spears | 604/21 |
| 4,589,404 | 5/1986 | Barath et al. | 128/6 |
| 4,612,938 | 9/1986 | Dietrich et al. | 128/665 |
| 4,625,724 | 12/1986 | Suzuki et al. | 128/303.1 |
| 4,643,186 | 2/1987 | Rosen et al. | 128/303.1 |
| 4,646,737 | 3/1987 | Hussein et al. | 128/303.1 |
| 4,660,925 | 4/1987 | McCaughan, Jr. | 350/96.15 |
| 4,662,368 | 5/1987 | Hussein et al. | 128/303.1 |
| 4,672,962 | 6/1987 | Hershenson | 128/303.1 |
| 4,676,231 | 6/1987 | Hisazami et al. | 128/303.1 |
| 4,693,556 | 9/1987 | McCaughan, Jr. | 350/320 |

FOREIGN PATENT DOCUMENTS 0182689 10/1985 European Pat. Off. .
2154761 9/1985 United Kingdom .

OTHER PUBLICATIONS

H. Fujii et al., "Light Scattering Properties of a Rough-Ended Optical Fibre", *Optics & Laser Technology*, Feb. '84.

Hiehle, Jr. et al., "Nd-YAG Laser Fusion of Human Atheromatous Plaque-Arterial Wall Separations in Vitro", *Am. J. Cardiol.*, vol. 56, Dec. 1, 1985, pp. 953-957.

*Primary Examiner*—Max Hindenburg
*Attorney, Agent, or Firm*—Wolf, Greenfield & Sacks

[57] ABSTRACT

A laser balloon catheter intended primarily for coronary angioplasty includes a flexible tube having an inflatable balloon secured to its distal end, a central shaft within the balloon for carrying a guide wire, an optical fiber for carrying laser radiation through the flexible tube into the balloon, and a tip assembly in the balloon for directing laser radiation outwardly through a major portion of the balloon surface while limiting shadowing by the central shaft. The tip assembly preferably includes a tip portion of the optical fiber contained within a transparent, heat-formable tube and formed into a spiral shape around the central shaft by the heat-formable tube. The optical fiber tip portion is tapered so that it directs laser radiation outwardly over its length. Deuterium oxide is preferably used for inflation of the balloon because of its very low attenuation of laser radiation in the wavelength range of interest. The disclosed laser balloon catheter is capable of delivering 30–40 watts of laser radiation to a surrounding artery for times on the order of 30 seconds without excessive heating of the balloon assembly.

47 Claims, 4 Drawing Sheets

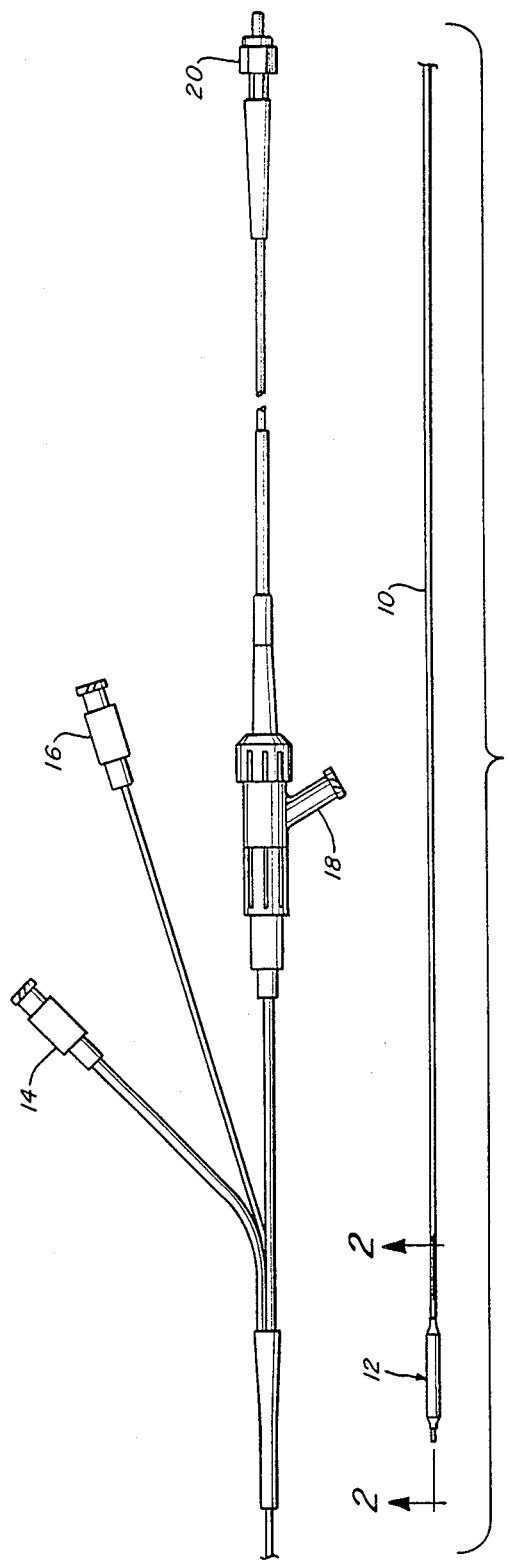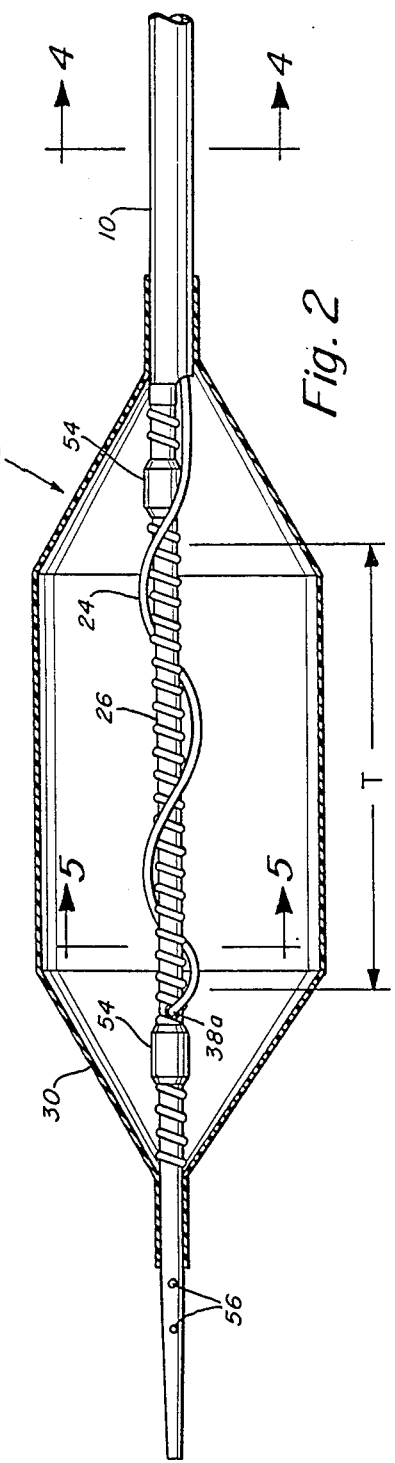

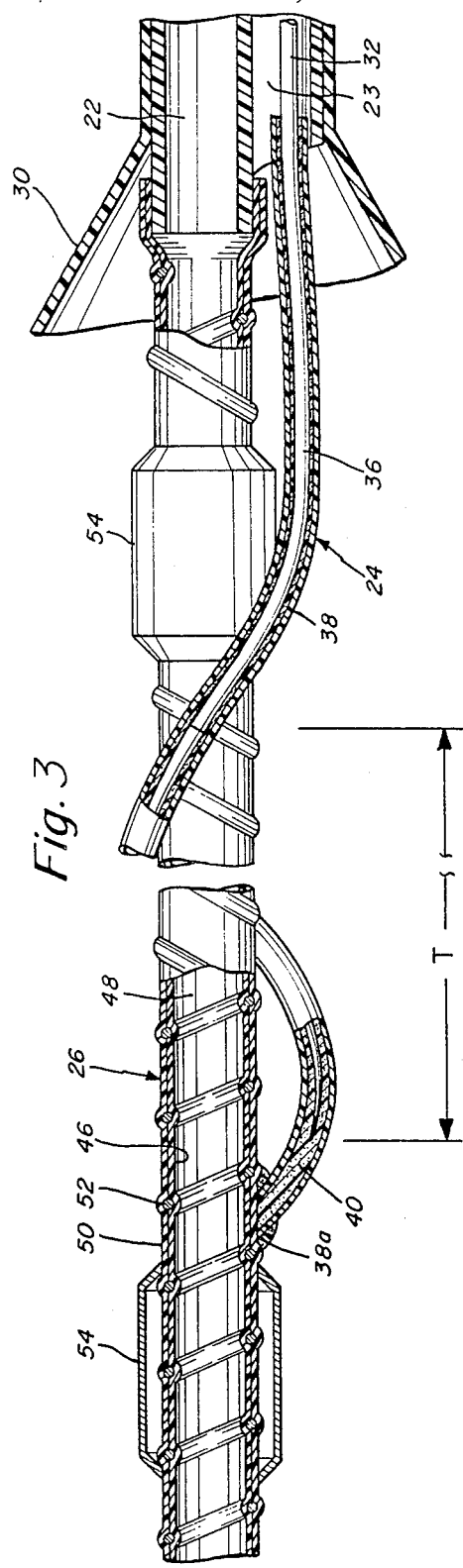
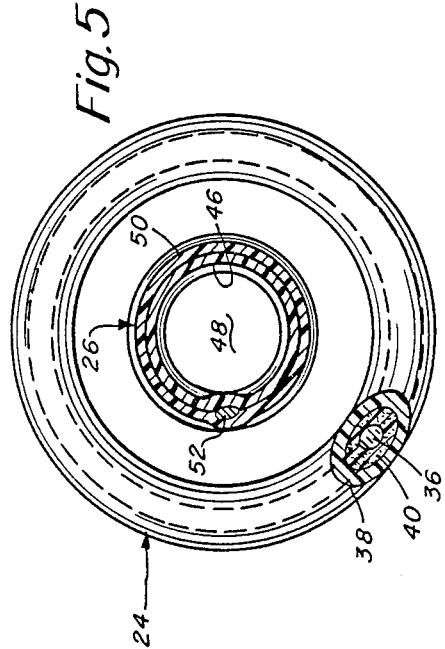
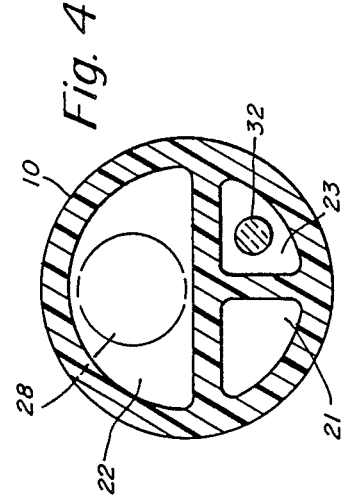

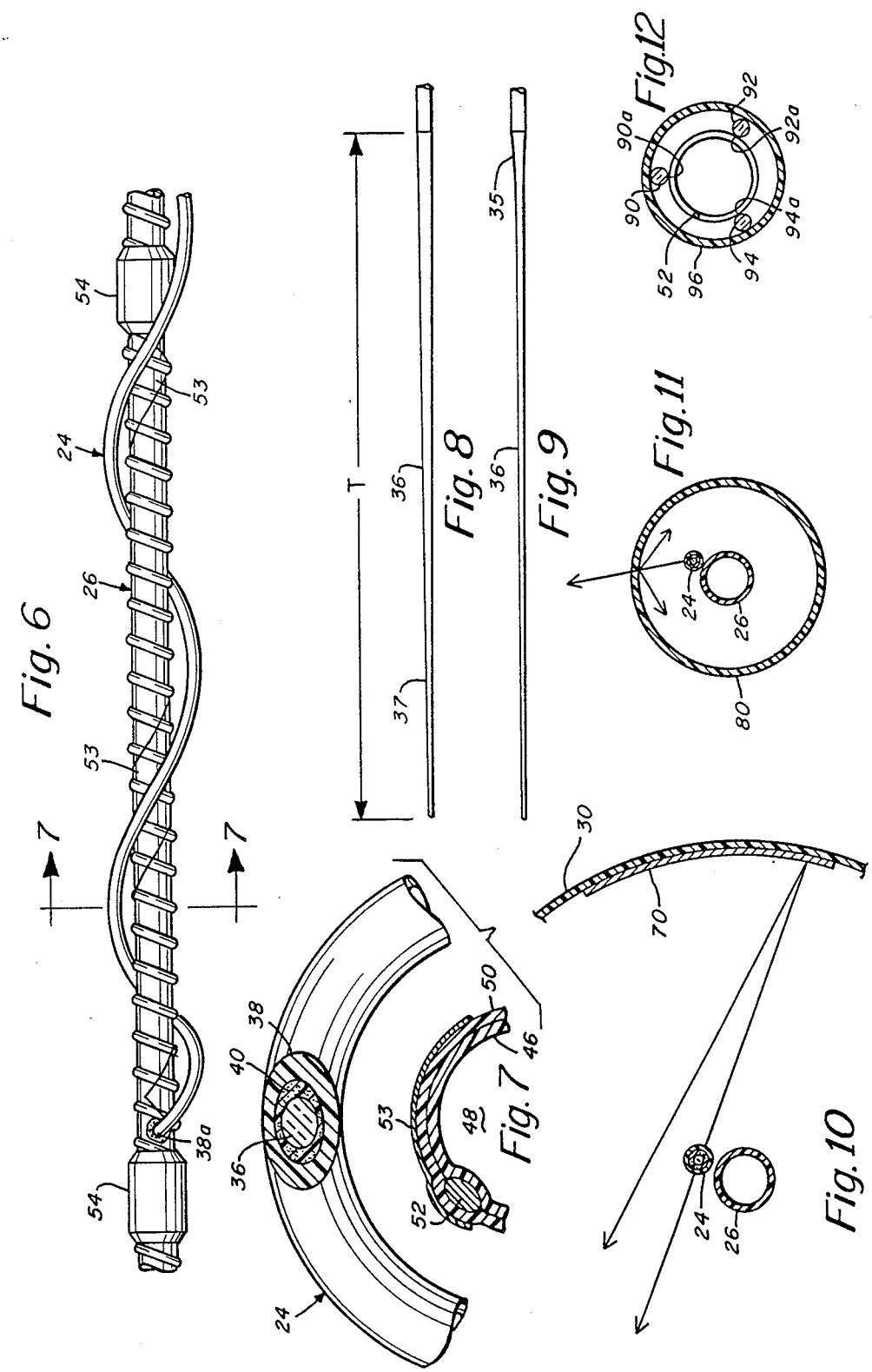

LASER BALLOON CATHETER

FIELD OF THE INVENTION

This invention relates to laser balloon catheters and to methods for the manufacture and use of laser balloon catheters and, more particularly, to laser balloon catheters intended for use with a guide wire and capable of providing a high level of laser output power through the balloon wall into surrounding tissue. The laser balloon catheter of present invention is intended primarily for coronary angioplasty, but is not limited to such use.

BACKGROUND OF THE INVENTION

Balloon angioplasty has been utilized for a number of years to treat coronary arteries narrowed by plaque deposits. A catheter having an inflatable balloon secured to its distal end is advanced through an artery to a narrowed region. The balloon is then inflated with a fluid from an external source, causing the narrowed region of the artery to be expanded. The balloon is then deflated and withdrawn. A serious problem associated with balloon angioplasty has been the occurrence in up to 30% of the cases of so-called restenosis, either immediately after the procedure or within about six months. Immediate restenosis, also known as abrupt reclosure, results from flaps or segments of plaque and plaque-ridden tissue which are formed during balloon angioplasty and which can block the artery. Such blockage of the artery requires emergency surgery and often results in death. Furthermore, a surgical team is required to stand by during the balloon angioplasty procedure. Restenosis at a later time results from causes that are not totally known. Thrombus formation is believed to play an important part. Often repeat balloon angioplasty or surgery is required, and another episode of restenosis may occur.

A technique which has shown great promise for overcoming the problem of restenosis is the simultaneous application of heat and pressure to a plaque-narrowed region of an artery. The technique is described by John F. Hiehle, Jr. et al in "Nd-YAG Laser Fusion of Human Atheromatous Plaque-Arterial Wall Separations in Vitro," *American Journal of Cardiology*, Vol. 56, Dec. 1, 1985, pp. 953-957. In accordance with this technique, a catheter having an inflatable balloon at its distal end is advanced to a narrowed region of an artery and the balloon is inflated, as in the case of balloon angioplasty. However, in distinction to balloon angioplasty, sufficient heat is applied through the wall of the balloon to fuse the surrounding tissue and thereby eliminate the flaps which can later block the artery. One advantageous means of heating the surrounding tissue is by directing laser radiation through an optical fiber carried by the catheter and terminating within the balloon. The laser radiation is then directed through the balloon wall to cause heating of the surrounding tissue.

Although the laser balloon catheter has been proposed in principle, there are numerous problems and difficulties in constructing a practical catheter suitable for human use. The balloon containing the device for diffusing laser radiation and the deflated catheter containing the optical fiber must be extremely flexible and small in diameter (on the order of 1.0 to 1.5 millimeters) in order to permit navigation of the catheter through an artery to the desired site. The laser balloon catheter is preferably compatible with a guide wire which is used to guide the catheter through the artery to the desired location. Where the guide wire passes through the balloon, shadowing of the laser radiation pattern by the guide wire must be avoided.

Another critical factor is the technique used for heating the surrounding tissue and the associated power level. It has been found desirable to apply radiation which penetrates the surrounding plaque and plaque-ridden tissue and the artery wall and heats that region by radiant heating, in distinction to conductive heating by the balloon. Furthermore, it has been found desirable to apply such radiation at a power level on the order of 30-40 watts for times of on the order of thirty seconds. With such high power levels, it is extremely critical to efficiently transfer the input laser radiation through the fluid which inflates the balloon and through the balloon wall with minimum heat dissipation within the balloon.

Other techniques involving the application of heat in a coronary artery include the so-called "hot tip" as disclosed in U.S. Pat. No. 4,646,737 issued Mar. 3, 1987 to Hussein et al and U.S. Pat. No. 4,662,368 issued May 5, 1987 to Hussein et al, wherein a thermally conductive tip located at the end of a catheter is heated by laser radiation and conducts heat to the surrounding region as it is pushed through a narrowed artery. The hot tip reaches temperatures on the order of several hundred degrees Celsius in order to produce the necessary conductive heating as it is pushed through the artery. The hot tip is unable to expand the artery beyond the conductive tip diameter, which must be limited for passage through the artery. Another heating technique wherein a microwave-radiating antenna is located within an inflatable balloon is disclosed in U.S. Pat. No. 4,643,186 issued Feb. 17, 1987 to Rosen et al. A coaxial transmission line is carried through a catheter and connects to the antenna.

An endoscopic device wherein low power, narrow beam laser radiation is directed through a balloon wall is disclosed in U.S. Pat. No. 4,470,407 issued Sept. 11, 1984 to Hussein. The problem of providing relatively uniform heating of tissue surrounding a balloon at high power levels and without shadowing is not addressed by the Hussein patent.

Prior art techniques have been disclosed for directing laser radiation outwardly from the tip of an optical fiber. A tapered optical fiber surrounded with a diffusing medium for laser radiation treatment of tumors is disclosed in U.K. Patent Application No. 2,154,761 published Sept. 11, 1985. An optical fiber surrounded with a scattering medium for producing a cylindrical pattern of light at the tip of an optical fiber is disclosed in U.S. Pat. No. 4,660,925 issued Apr. 28, 1987 to McCaughan, Jr. A technique for roughening the surface of an optical fiber tip to cause wide angle radiation of laser energy is disclosed by H. Fujii et al, "Light Scattering Properties of A Rough-ended Optical Fiber," *Optics and Laser Technology*, February 1984, pp. 40-44. None of the prior art techniques provide the combination of small diameter, flexibility, power handling capability and compatibility with a guide wire necessary for a laser balloon catheter.

It is a general object of the present invention to provide an improved laser balloon catheter.

It is a further object of the present invention to provide a laser balloon catheter suitable for use in coronary angioplasty.

It is another object of the present invention to provide a laser balloon catheter capable of delivering and surviving a high power output.

It is another object of the present invention to provide a laser balloon catheter which can be utilized with a guide wire for advancing the catheter through an artery.

It is another object of the present invention to provide a laser balloon catheter which produces substantially uniform heating of tissue surrounding the balloon.

It is still another object of the present invention to provide a method for manufacturing a laser balloon catheter.

It is yet another object of the present invention to provide a laser balloon catheter which is small in diameter and flexible so that it is easily advanced through an artery.

It is yet another object of the present invention to provide a laser balloon catheter wherein heat dissipation of laser radiation within the balloon is limited to allow heating deep into an artery wall without excessive total energy.

It is a further object of the present invention to provide a laser balloon catheter wherein a relatively high proportion of the input laser radiation is delivered through the balloon wall to the surrounding tissue.

SUMMARY OF THE INVENTION

According to the present invention, these and other objects and advantages are achieved in a laser balloon catheter comprising an elongated flexible tube having a distal end and a proximal en, an inflatable balloon secured to the flexible tube at or near the distal end thereof, means for inflating and deflating the balloon, a central shaft disposed within the balloon and coupled to the flexible tube, an optical fiber for carrying laser radiation through the flexible tube into the balloon, and tip assembly means in the balloon and coupled to the optical fiber for directing laser radiation outwardly through a major portion of the balloon area while limiting shadowing by the central shaft.

Preferably, the tip assembly means includes a tip portion of the optical fiber which is tapered to a smaller diameter at the distal end thereof and shaping means for retaining the tip portion of the optical fiber in a shape having at least one turn around the central shaft. The tip portion of the optical fiber preferably has a generally spiral shape. In a preferred embodiment, the shaping means includes a heat-formable tube containing the tip portion of the optical fiber and a material located between the heat-formable tube and the tip of the optical fiber selected to match the indices of refraction of the heat-formable tube and the tip portion. The spiral tip portion of the optical fiber is flexible and emits laser radiation outwardly over its length while limiting shadowing by the central shaft.

Preferably, the central shaft, which is typically used for carrying a guide wire, includes an inner tube, a concentric outer tube and a spring coil between the inner and outer tubes. The spring coil prevents the central shaft from collapsing when the balloon is inflated. The central shaft includes a laser radiation-reflecting outer surface such as white vinyl or a thin layer of gold disposed on the outer tube.

In another important aspect of the invention, a laser balloon catheter is inflated with a liquid which attenuates laser radiation at the wavelength of interest less than saline in order to limit heat dissipation within the balloon and to increase output power. Preferably, the liquid has an attenuation of less than about 0.16/cm at a preferred laser wavelength of 1.06 micrometer. In a preferred embodiment, the balloon is inflated with deuterium oxide for reduced absorption of laser radiation in comparison with conventional inflation fluids such as saline or water. The deuterium oxide absorbs a negligible amount of energy at the preferred laser wavelength of 1.06 micrometer. Deuterium oxide can be advantageously used in any laser balloon catheter to reduce energy absorption and is not limited to the laser balloon catheter described herein. The deuterium oxide is biologically safe and is preferably utilized in conjunction with a transparent PET balloon.

According to other features of the invention, a dye responsive to laser radiation of a predetermined first wavelength for emitting radiation at a predetermined second wavelength, and a dye solvent, can be mixed in the inflation fluid. The inflation fluid can contain a contrast agent to facilitate location of the balloon during use. A material with thermally sensitive optical properties can also be mixed in the inflation fluid for monitoring the temperature of the balloon along the optical fiber. An inwardly-facing reflector can be provided on a portion of the balloon to control the heating pattern produced by the laser radiation.

According to another aspect of the present invention, there is provided a method of operating a laser balloon catheter comprising the steps of advancing a catheter having an inflatable balloon secured at or near its distal end and having an optical fiber terminating within the balloon through a body passage to a desired treatment location, inflating the balloon with a low attenuation liquid such as deuterium oxide and directing laser radiation through the optical fiber into the balloon such that the radiation passes through the low attenuation liquid and the balloon for treatment.

According to still another aspect of the present invention, there is provided a method of making an optical fiber tip assembly for emitting laser radiation outwardly therefrom along its length comprising the steps of providing an optical fiber having a tapered tip portion, inserting the tapered tip portion into a transparent tube and filling the space between the transparent tube and the tapered tip portion with a material that is selected to match the indices of refraction of the transparent tube and the tip portion. Preferably, the transparent tube is heat-formable and the method further includes the step of preforming the transparent tube to a desired shape. The step of filling the space between the transparent tube and the tip portion preferably includes the steps of immersing a silicon tube in freon to cause expansion thereof, slipping the expanded silicon tube over the transparent tube, permitting the silicon tube to contract to its normal size and injecting the material from a syringe through the silicon tube into the transparent tube.

According to still another aspect of the invention, there is provided a method of making a laser balloon catheter comprising the steps of forming a spiral tip assembly at one end of an optical fiber, providing a flexible tube having a distal end and a proximal end and having at least two lumens therethrough, attaching a central shaft for carrying a guide wire to the distal end of the flexible tube so that a passage through the central shaft is aligned with one of the lumens, inserting the optical fiber through another of the lumens so that the spiral tip assembly is disposed at the distal end of the flexible tube around the central shaft, and sealing an inflatable balloon to the distal end of the flexible tube around the spiral tip assembly and the central shaft.

In another embodiment of the tip assembly, a transverse optical waveguide surrounds the optical fiber and the central shaft. The transverse waveguide directs a portion of the laser radiation around the central shaft and limits shadowing.

In yet another embodiment of the tip assembly, one or more optical fibers are stressed at multiple points by pressing them against a spring coil in the central shaft. The regions of stress emit laser radiation outwardly.

BRIEF DESCRIPTION OF THE DRAWINGS

For a better understanding of the present invention together with other and further objects, advantages and capabilities thereof, reference is made to the accompanying drawings which are incorporated herein by reference and in which:

FIG. 1 is a fragmented illustration of a laser balloon catheter in accordance with the present invention;

FIG. 2 is an enlarged cross-sectional view of the distal end of the laser balloon catheter taken along the lines 2—2 of FIG. 1;

FIG. 3 is an enlarged, fragmented view, partly in cross-section, of the central shaft and optical fiber tip assembly;

FIG. 4 is an enlarged cross-sectional view taken along the lines 4—4 of FIG. 2 showing the catheter lumens;

FIG. 5 is an enlarged, cross-sectional view of the central shaft and optical fiber tip assembly taken along the lines 5—5 of FIG. 2;

FIG. 6 is an enlarged illustration of the optical fiber tip assembly and a central shaft having a gold reflecting layer;

FIG. 7 is an enlarged, partial cross-sectional view taken along the lines 7—7 of FIG. 6;

FIGS. 8 and 9 illustrate optical fiber tips having different taper rates;

FIG. 10 illustrates a laser balloon with an inwardly-reflecting surface;

FIG. 11 illustrates a tip assembly utilizing transverse waveguiding to limit shadowing; and FIG. 12 illustrates a tip assembly utilizing microbending of optical fibers and FIG. 13 illustrates a laser balloon catheter having a double balloon arrangement.

DETAILED DESCRIPTION OF THE INVENTION

Figure 13:
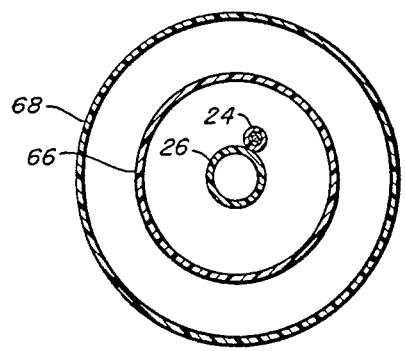

A laser balloon catheter in accordance with a preferred embodiment of the invention is shown in FIGS. 1-5. An elongated flexible tube 10 has a laser balloon assembly 12 at its distal end and connectors 14, 16, 18 and 20 at its proximal end. The flexible tube 10 preferably includes three lumens 21, 22 and 23 (FIG. 4). The laser balloon assembly 12 includes an optical fiber tip assembly 24 (FIG. 2) for emitting laser radiation, a central shaft 26 adapted for carrying a guide wire 28 (shown in phantom in FIG. 4) and for carrying a fluid to the treatment region and a balloon 30 which is inflated and deflated from the proximal end of the flexible tube 10.

An optical fiber 32 extends from connector 20 through lumen 23 of the flexible tube 10 and terminates in optical fiber tip assembly 24. Connector 20 is coupled to the output of a laser. The guide wire 28 is introduced into the catheter through connector 16 and passes through lumen 22 of flexible tube 10 and through central shaft 26, which is coupled to lumen 22. A source of pressurized fluid is coupled through connector 14 and lumen 21 to the interior of balloon 30. Means for evacuating the balloon are also coupled through connector 14 and lumen 21 to the interior of balloon 30. Connector 18 is a vent port coupled to the balloon via lumen 23.

As shown in FIGS. 3 and 5, the optical fiber tip assembly 24 includes a tip portion 36, a transparent tube 38 surrounding the tip portion 36 and a transparent epoxy 40 that fills the space between transparent tube 38 and tip portion 36. The tip portion 36 is preferably a continuation of optical fiber 32.

Tip portion 36 is tapered over a distance T in order to cause laser radiation to be directed outwardly in a transverse or radial direction relative to the catheter axis. It is known in the art that a tapered optical fiber causes light to be gradually directed outwardly since the critical angle for reflected rays is gradually exceeded. In a preferred embodiment, an optical fiber type SG822 from Spectran Corporation, having a 150 micrometer outer diameter and a 100 micrometer core diameter, is tapered over a tip portion length of about 2 centimeters. The fiber is tapered from full diameter at the proximal end of the tip portion 36 to essentially zero diameter, or a few micrometers diameter, at the distal end.

Tapering of the optical fiber tip portion 36 is accomplished using hydrofluoric acid as an etchant. The fiber 32 is placed in the etching solution and is withdrawn at a controlled rate under computer control. In a preferred embodiment, a uniform taper is obtained by withdrawing the fiber from the etching solution at a constant rate. In other embodiments, the taper is nonuniform in order to control the axial light intensity distribution. The light intensity emitted by the fiber is relatively high in a region with a high rate of taper and is relatively low in a region with a low rate of taper. For example, the rate of taper can be greatest near the proximal end 35 of tip portion 36, as shown in FIG. 9, so that the emitted light intensity is increased near the proximal end of the balloon. Alternatively, the rate of taper can be greatest near the distal end 37 of the tip portion 36, as shown in FIG. 8, thereby increasing the light intensity at the distal end of the balloon. In general, the axial light intensity distribution is tailored by controlling the rate of optical fiber taper.

Another important feature of the optical fiber tip assembly 24 is that it preferably has a spiral or helical configuration extending around central shaft 26 so that shadowing by central shaft 26 is minimized. While the tip assembly 24 can have any convenient shape, it should have at least one full turn around central shaft 26 in order to minimize shadowing. The gradually-curving spiral shape avoids sharp turns which are likely to break the optical fiber 32. In a preferred embodiment, the tip assembly 24 makes two full turns around the shaft 26 over a distance of about 2 centimeters.

Presently available optical fibers cannot be formed to retain the desired spiral shape. In addition, it is desirable that the tip portion 36 be relatively free to move and flex within the balloon in order to facilitate passage of the catheter through an artery. The transparent tube 38 performs the functions of shaping the tip portion 36 of the optical fiber to the desired spiral shape and also acts as a replacement for the protective optical fiber buffer which was removed during the tapering process. It has been found that the tapered tip portion 36 must have a relatively smooth surface to prevent fiber breakage.

Although optical fibers with roughened surfaces have been used as diffusion tips, such roughened fibers have been found likely to break in a catheter application requiring flexibility. The transparent tube 38 is preferably a heat-formable tube and, most preferably, is polyethyleneterephthalate (PET). The PET tube is formed by wrapping it around a mandrel in the desired spiral shape and heating it to a temperature of about 200° C. After cooling, the PET tube retains the spiral shape.

The tapered tip portion 36 of the optical fiber is then inserted into the spiral transparent tube 38, and the space between the tube 38 and tip portion 36 is filled with an optically transparent material selected to match the indices of refraction of tube 38 and tip portion 36. Preferably, an optically transparent epoxy such as Environ/Tex Lite is utilized. In a preferred technique for injecting the epoxy 40 into the tube 38, a length of silicon tubing, smaller in diameter than tube 38, is dipped in freon. The freon causes the silicon tube to swell, permitting it to be slipped over one end of transparent tube 38. After removal from the freon, the silicon tube shrinks and forms a tight fit over the PET tube 38. The other end of the silicon tube is attached to a syringe containing the epoxy. Upon operation of the syringe, the epoxy is injected through the silicon tube into the PET tube 38 and is allowed to cure. The silicon tube is then removed from the end of the transparent tube 38.

The central shaft 26 provides a passage for guide wire 28. The proximal end of central shaft 26 is coupled to lumen 22 of flexible tube 10. The central shaft 26 must be relatively incompressible to prevent its collapse when the balloon 30 is inflated. In a preferred embodiment shown in FIGS. 3 and 5, the central shaft 26 includes an inner vinyl tube 46 having a passage 48 for guide wire 28, an outer vinyl tube 50 concentric with tube 46 and a spring coil 52 located between tubes 48 and 50. The spring coil 52 is preferably 0.001 in. × 0.003 in. stainless steel wire frequently used in guide wire catheters. The assembly comprising tubes 48 and 50 and spring coil 52 is heated to a temperature of about 150° so as to cause elastic flow of the vinyl tubes 48, 50 between the turns of the spring coil 52. The spring coil 52 prevents the shaft 26 from collapsing on guide wire 28 when balloon 30 is inflated.

The outer surface of vinyl tube 50 should have high reflectivity at the selected laser wavelength in order to prevent absorption of laser radiation and heating of central shaft 26. The use of a white vinyl tube 50 provides the necessary reflectivity over a broad band of wavelengths. In another preferred embodiment as shown in FIGS. 6 and 7, a thin layer of gold leaf 53 is applied to the outer surface of vinyl tube 50 for improved reflectivity. The gold leaf 53 can have a spiral configuration around the vinyl tube 50 which matches the spiral shape and is located adjacent to optical fiber tip assembly 24. Thus, the portion of central shaft 26 adjacent to tip assembly 24 has a highly reflective gold surface. Alternatively, the entire shaft 26 can be coated with gold. An advantage of the gold surface is that it is radiopaque and can be used for x-ray location of the balloon assembly 12.

The central shaft 26 is further provided with a pair of spaced-apart radiopaque markers 54. The markers 54, which can be platinum bands around shaft 26, can be seen in an x-ray so that the balloon assembly 12 can be precisely located during use. The shaft 26 is further provided with one or more openings 56 near its distal end for introduction of a fluid into the treatment region via connector 16.

The inflatable balloon 30 has a generally tubular shape. It is sealed at one end at or near the distal end of flexible tube 10 and is sealed at its other end to central shaft 26 as shown in FIG. 2. The balloon 30 is optically transparent at the selected wavelength of the laser radiation. Preferably, a PET balloon is utilized. PET has a number of characteristics which make it a suitable balloon material. These characteristics include good optical transparency and a thin wall to reduce the overall catheter cross section and also to reduce heat absorption. In addition, PET does not deform at elevated temperatures and does not stick to the tissue being treated. In one embodiment, a balloon which inflates to 3 millimeters is used. It will be understood that the inflated diameter of the balloon is selected in accordance with the cross-sectional area of the body passage being treated.

In a preferred embodiment, a 40 watt neodymium YAG continuous laser is used as the source of laser radiation. This laser has an output wavelength of 1.06 micrometer. Typical treatment times are on the order of 30 seconds. The 1.06 micrometer wavelength has been selected for its ability to penetrate the plaque and plaque-ridden tissue and the artery wall and to cause deep heating of such tissue, rather than to simply heat the tissue surface. Thus, heating of the tissue surrounding balloon 30 is by radiation as contrasted with conductive heating from a hot element. One object of the present laser balloon catheter configuration is to reduce heat dissipation within balloon 30.

A relatively high level of laser power is required to be transferred through the optical fiber 32 and the laser balloon assembly 12. Accordingly, it is important to minimize absorption of laser radiation within the laser balloon assembly 12 in order to minimize melting, burning and other detrimental effects of the high power levels. In accordance with an important aspect of the present invention, the balloon 30 is inflated with a liquid having an attenuation at the laser wavelength of interest less than that of commonly-used saline. Preferably, the balloon inflation liquid has an attenuation less than about 0.16/cm at a wavelength of 1.06 micrometer. It has been found that the heat dissipation within the balloon assembly 12 can be substantially reduced by utilizing deuterium oxide ($D_2O$) as the fluid for inflation of the balloon 30. Deuterium oxide has substantially lower absorption at the 1.06 micrometer wavelength of interest than prior art inflation fluids such as saline or water. A 3 millimeter diameter laser balloon catheter filled with deuterium oxide transmits approximately 90% of the input laser radiation at 1.06 micrometer, whereas the same catheter filled with water transmits approximately 80% of the laser radiation. Relatively low absorption is characteristic of deuterium oxide at wavelengths in the range between 0.9 and 1.8 micrometers. As a result, heat dissipation within the balloon 30 is reduced by a factor of one-half by using deuterium oxide for inflation.

Additional advantages of deuterium oxide as the balloon inflation fluid include the ability to use a larger diameter balloon without exceeding a prescribed power dissipation limit and more light output for a given laser input. Furthermore and importantly, deuterium oxide is biologically safe for use in the human body. It will be understood by those skilled in the art that the use of deuterium oxide for balloon inflation is not limited to the laser balloon catheter structures described herein, but can be utilized in any inflatable balloon wherein it is desired to transmit radiation in the above-identified wavelength range.

In order to assemble the laser balloon catheter of the present invention, the optical fiber tip assembly 24 and the central shaft 26 are fabricated as described hereinabove. The central shaft 26 is heat bonded to the end of flexible tube 10 so that passage 48 is aligned with lumen 22. Next, optical fiber 32 is fed through lumen 23 of flexible tube 10 starting at the distal end thereof so that the spiral tip assembly 24 surrounds central shaft 26. The distal end 38a of transparent tube 38 is bonded to shaft 26 with cynoacrylate in order to fix their relative positions. Otherwise, the tip assembly 24 and shaft 26 may contact each other along their lengths but are not attached. This configuration maintains the flexibility of the central shaft 26 and tip assembly 24. The spiral tip assembly 24 has more flexibility and less risk of breakage than a straight segment of optical fiber. The balloon 30 is sealed at its proximal end to the flexible tube 10 and is sealed at its distal end to the central shaft 26.

The interior of the balloon 30 is in fluid communication with lumen 21 of flexible tube 10 for inflation and deflation and with lumen 23 for venting. The use of lumen 21 in conjunction with vent lumen 23 permits the catheter to be purged of air bubbles. Connectors 14, 16, 18 and 20 are installed at the proximal end of flexible tube 10 in conventional manner.

In use, the laser balloon catheter of the present invention and an associated guide wire 28 are advanced through an artery to a desired treatment location, typically, a narrowed region of a coronary artery. It will be understood that in some applications, a guide wire will not be necessary and that the laser balloon catheter of the present invention can be utilized without a guide wire. The precise location of the balloon assembly is determined by identifying markers 54 on an x-ray. The balloon 30 is then inflated by filling it with deuterium oxide carried through lumen 21 of flexible tube 10. After balloon inflation, the laser is energized, causing laser radiation to be carried through optical fiber 32 and tip assembly 24 into the balloon. The laser radiation passes through transparent balloon 30 and irradiates the tissue surrounding balloon 30 with a substantially uniform heating pattern. The heating causes the surrounding plaque and plaque-ridden tissue to be fused to the artery walls so that flaps and segments are not formed. Although the clinical aspects of the treatment are outside the scope of the present invention, it will be understood that an enlarged passage is formed in the artery with the walls of the passage being fused into a generally cylindrical and continuous configuration. The laser radiation is applied for a time on the order of about thirty seconds. After laser radiation has been completed, the region is allowed to cool and the balloon 30 is evacuated through lumen 21 and the catheter is removed.

It will be understood that numerous variations and features can be incorporated into the laser balloon catheter of the present invention. For example, various materials can be mixed with the fluid utilized to inflate the balloon 30. As described above, deuterium oxide is the preferred inflation fluid, but water or saline can be used in applications requiring moderate or low power levels. Also, any other fluid having sufficiently low attenuation and suitable biological compatibility can be utilized. Radiopaque iodine-based contrast media can be mixed with the fluid used for inflation of the balloon.

The contrast media permits the size, shape and location of the inflated balloon to be determined by x-ray.

In another variation, materials having optical properties that change with temperature can be mixed with the inflation fluid. An example of such material is liquid crystals. A color change can be sensed through the optical fiber for monitoring of the balloon temperature. If the balloon temperature exceeds a predetermined limit, the laser beam can be turned off.

In yet another variation, a laser dye material such as rhodamine is mixed with the fluid used to inflate the balloon. The laser dye material absorbs radiation at the wavelength of the laser source and emits radiation at a different wavelength. Alternatively, the laser dye can be mixed with the epoxy 40 in the space between the tip portion 36 of the optical fiber and the transparent PET tube 38. In either case, the laser dye material changes the wavelength of the laser output wavelength to another desired wavelength more suitable for treatment.

The laser balloon catheter of the present invention has been described primarily in connection with coronary angioplasty. It will be understood by those skilled in the art that the laser balloon catheter, with appropriate scaling of dimensions when necessary, can be utilized in any body passage requiring the simultaneous application of heat and pressure. One example of such an application is the treatment of cancer in various body passages. When a larger diameter balloon is required, a double balloon arrangement can be utilized. As shown in FIG. 13, an inner balloon 66 of relatively small diameter is filled with deuterium oxide or water, and a concentric outer balloon 68 of larger diameter is inflated with air. It may be desirable under some circumstances to heat a sector or portion of a body passage rather than providing uniform heat. In such a case, an inwardly-facing reflecting layer 70 is applied to a portion of the balloon surface as shown in FIG. 10. Where the reflecting layer 70 is present, the laser radiation is reflected through the opposite balloon wall. In this manner, a desired radial heating pattern can be accomplished.

According to another embodiment of the present invention, a transverse waveguiding technique is utilized to provide substantially uniform laser radiation output from the balloon when a guide wire is used. In this embodiment, the tip portion of the optical fiber can be straight, can have a spiral shape as described above or can have some other convenient shape. A transverse waveguide 80 surrounds both the optical fiber tip assembly 24 and the central shaft 26 as shown in FIG. 11. The transverse waveguide 80 can, for example, be a partially transmissive tube with a scattering material on its inner surface. Laser radiation emitted by the optical fiber tip assembly 24 impinges on the interior surface of the transverse waveguide 80. A fraction of the incident laser radiation passes through the transverse waveguide 80 and another fraction is guided in a circumferential direction around the central shaft and optical fiber tip assembly 24. Eventually, all of the incident laser radiation passes through the transverse waveguide with a generally uniform radial pattern, thereby avoiding shadowing by the central shaft 26.

According to yet another embodiment of the present invention, a technique utilizing microbending of one or more optical fibers within the balloon provides laser radiation outwardly through the wall of the balloon. It is known that optical fibers emit light outwardly at points of stress and bending. In the present embodiment, optical fibers 90, 92, 94 are oriented more or less parallel to the spring coil 52 within the balloon 30 and are pressed against it, as shown in FIG. 12, by an optically transparent, heat shrinkable tube 96. At each turn of spring coil 52, a stress is applied to each of the optical fibers 90, 92, 94, and laser radiation is emitted at each stress point 90a, 92a, 94a. More or fewer optical fibers can be utilized. Furthermore, some, all or none of the optical fibers 90, 92, 94 can be selectively energized at a given instant of time to control the laser radiation pattern and timing.

While there has been shown and described what is at present considered the preferred embodiments of the present invention, it will be obvious to those skilled in the art that various changes and modifications may be made therein without departing from the scope of the invention as defined by the appended claims.

What is claimed is:

1. A laser balloon catheter comprising:
    an elongated flexible tube having a distal end and a proximal end;
    an inflated balloon secured to said flexible tube at or near the distal end thereof;
    means for inflating and deflating said balloon;
    central shaft means disposed in said balloon and coupled to said flexible tube;
    an optical fiber for carrying laser radiation through said flexible tube into said balloon; and
    tip assembly means coupled to said optical fiber for directing laser radiation outwardly through a major portion of the balloon surface, said tip assembly means being located within said balloon between said central shaft means and the balloon surface and including means for limiting shadowing thereof by said central shaft means.

2. A laser balloon catheter as defined in claim 1 wherein said tip assembly means includes a tip portion of said optical fiber and shaping means for retaining the tip portion of said optical fiber in a desired shape having at least one turn around said shaft means.

3. A laser balloon catheter as defined in claim 2 wherein said shaping means comprises a heat-formable tube containing the tip portion of said optical fiber.

4. A laser balloon catheter as defined in claim 3 wherein said shaping means further comprises a material located between said heat-formable tube and the tip of said optical fiber and selected to match the indices of refraction of said heat-formable tube and said tip portion.

5. A laser balloon catheter as defined in claim 2 wherein said shaping means comprises a PET tube heat formed to the desired shape and containing the tip portion of said optical fiber.

6. A laser balloon catheter as defined in claim 5 wherein said shaping means further includes epoxy between said PET tube and said tip portion.

7. A laser balloon catheter as defined in claim 5 wherein said PET tube is attached at its distal end to said catheter shaft means.

8. A laser balloon catheter as defined in claim 2 wherein said tip portion of said optical fiber is tapered to a smaller diameter at the distal end thereof.

9. A laser balloon catheter as defined in claim 8 wherein he tip portion of said optical fiber has a uniform taper.

10. A laser balloon catheter as defined in claim 8 wherein the tip portion of said optical fiber has a greater rate of taper near the distal end thereof.

11. A laser balloon catheter as defined in claim 8 wherein the tip portion of said optical fiber has a greater rate of taper near the proximal end thereof.

12. A laser balloon catheter as defined in claim 2 wherein the tip portion of said optical fiber has a spiral shape.

13. A laser balloon catheter as defined in claim 1 wherein said central shaft means includes a laser radiation reflecting outer surface.

14. A laser balloon catheter as defined in claim 2 wherein said tip portion of said optical fiber includes about one full turn per centimeter around said central shaft means.

15. A laser balloon catheter as defined in claim 1 wherein said inflatable balloon is made of PET.

16. A laser balloon catheter as defined in claim 1 wherein said central shaft means comprises an inner tube, a concentric outer tube and a spring coil between said inner and outer tubes.

17. A laser balloon catheter as defined in claim 1 further including a gold layer disposed on an outer surface of said central shaft means for reflecting laser radiation.

18. A laser balloon catheter as defined in claim 17 wherein said gold layer is disposed on the outer surface of said central shaft means in a pattern generally matching the shape of the tip portion of said optical fiber.

19. A laser balloon catheter as defined in claim 1 wherein said flexible tube includes a first lumen for inflating and deflating the inflatable balloon, a second lumen for carrying said optical fiber and for venting air bubbles, and a third lumen for carrying a guide wire.

20. A laser balloon catheter as defined in claim 1 wherein said means for inflating and deflating said balloon includes means for inflating said balloon with a liquid having an attenuation of said laser radiation in a wavelength range between 0.9 and 1.8 micrometers that is less than the attenuation of saline.

21. A laser balloon catheter as defined in claim 1 wherein said means for inflating and deflating said balloon includes means for inflating said balloon with deuterium oxide.

22. A laser balloon catheter as defined in claim 21 wherein said laser radiation is in a wavelength range between 0.9 and 1.8 micrometers.

23. A laser balloon catheter as defined in claim 1 wherein said means for inflating and deflating said balloon includes means for inflating said balloon with infusate containing a dye dissolved in a solvent, said dye being responsive to said laser radiation of a first predetermined wavelength for emitting radiation at a second predetermined wavelength.

24. A laser balloon catheter as defined in claim 1 wherein said tip assembly means comprises a tip portion of said optical fiber and waveguide means surrounding said shaft means and said tip portion of said optical fiber for directing laser radiation circumferentially around said shaft means.

25. A laser balloon catheter as defined in claim 1 further including an inwardly-facing reflector on a portion of said balloon.

26. A laser balloon catheter as defined in claim 1 wherein said central shaft means includes a spring coil having multiple, relatively-rigid turns and wherein said tip assembly means comprises at least one optical fiber and means for pressing said optical fiber against the turns of said spring coil so that laser radiation is emitted from regions of contact between said spring coil and said optical fiber.

27. A laser balloon catheter as defined in claim 1 wherein said means for inflating and deflating said balloon includes means for inflating said balloon with a fluid containing a contrast media.

28. A laser balloon catheter as defined in claim 1 wherein said means for inflating and deflating said balloon includes means for inflating said balloon with a fluid containing a material with thermally-sensitive optical properties for temperature monitoring.

29. A laser balloon catheter as defined in claim 1 further including a second balloon surrounding said first-mentioned balloon and means for inflating said second balloon with gas.

30. A laser balloon catheter comprising:
   an elongated flexible tube having a distal end and a proximal end;
   an inflatable balloon secured to said flexible tube at or near the distal end thereof;
   an optical fiber for carrying laser radiation through said flexible tube into said balloon; and
   means for inflating said balloon with deuterium oxide.

31. A laser balloon catheter as defined in claim 30 wherein said optical fiber includes a tip portion for emitting laser radiation outwardly therefrom along its length and through said deuterium oxide.

32. A laser balloon catheter as defined in claim 31 wherein said inflatable balloon is made of PET.

33. A laser balloon catheter as defined in claim 30 further including means coupled to said optical fiber and disposed within said balloon for directing laser radiation carried by said optical fiber outwardly through said deuterium oxide and said balloon.

34. A laser balloon catheter as defined in claim 30 wherein said laser radiation is in a wavelength range between 0.9 and 1.8 micrometers.

35. A laser balloon catheter as defined in claim 31 wherein the tip portion of said optical fiber is tapered from a larger diameter at its proximal end to a smaller diameter at its distal end.

36. A laser balloon catheter as defined in claim 30 wherein said means for inflating and deflating said balloon includes means for inflating said balloon with a fluid containing a laser dye responsive to said laser radiation of a first predetermined wavelength for emitting radiation at a second predetermined wavelength.

37. A method of operating a laser balloon catheter comprising the steps of:
   advancing a catheter having an inflatable balloon secured at or near its distal end and having an optical fiber terminating within the balloon through a body passage to a desired treatment location;
   inflating the balloon with deuterium oxide; and
   directing laser radiation through said optical fiber into said balloon such that the radiation passes through said deuterium oxide and said balloon for treatment.

38. A method of operating a laser balloon catheter as defined in claim 37 wherein the step of directing laser radiation includes directing laser radiation in a wavelength range between 0.9 and 1.8 micrometers so that the radiation passes through the deuterium oxide and the balloon without substantial absorption for heating of the surrounding tissue.

39. A method of operating a laser balloon catheter as defined in claim 38 wherein the step of directing laser radiation includes directing the laser radiation so as to produce substantially uniform heating of the body passage in a region surrounding the balloon.

40. A method of operating a laser balloon catheter as defined in claim 37 wherein the step of inflating the balloon includes inflating the balloon with solvent containing a laser dye responsive to said laser radiation of a first predetermined wavelength for emitting radiation at a second predetermined wavelength.

41. A method for operating a laser balloon catheter as defined in claim 37 wherein the step of inflating the balloon includes inflating the balloon with deuterium oxide containing a contrast agent.

42. A method of operating a laser balloon catheter as defined in claim 37 wherein the step of inflating the balloon includes the step of inflating the balloon with deuterium oxide containing a material with thermally-sensitive optical properties for temperature monitoring.

43. A laser balloon catheter comprising:
   an elongated flexible tube having a distal end and a proximal end;
   an inflatable transparent balloon secured to said flexible tube at or near the distal end thereof;
   means for inflating and deflating said balloon;
   a relatively incompressible central tube located in said balloon and coupled to said flexible tube for carrying a guide wire; and
   an optical fiber for carrying laser radiation through said flexible tube into said balloon, said optical fiber including a tip portion in said balloon for emitting laser radiation outwardly therefrom through a major portion of the balloon, said tip portion extending around said central tube in a spiral configuration having at least one complete turn.

44. A laser balloon catheter as defined in claim 43 further including shaping means for retaining said tip portion of said optical fiber in said spiral configuration.

45. A laser balloon catheter as defined in claim 44 wherein said tip portion of said optical fiber is tapered to a smaller diameter at the distal end thereof.

46. A laser balloon catheter as defined in claim 45 wherein said shaping means comprises a preformed transparent tube containing the tip portion of said optical fiber and a material between said transparent tube and said tip portion selected to match the indices of refraction of said transparent tube and said tip portion.

47. A laser balloon catheter as defined in claim 46 wherein the material between said transparent tube and said tip portion contains a laser dye responsive to laser radiation of a first predetermined wavelength for emitting radiation at a second predetermined wavelength.

* * * * *